United States Patent [19]

Broom et al.

[11] Patent Number: 4,774,238

[45] Date of Patent: Sep. 27, 1988

[54] HETEROCYCLIC-METHYLENE-PENEMS

[75] Inventors: Nigel J. P. Broom, Billingshurst; Anthony C. Marshall, Dorking, both of England

[73] Assignee: Beecham Group plc, Middlesex, England

[21] Appl. No.: 887,270

[22] Filed: Jul. 21, 1986

[30] Foreign Application Priority Data

Jul. 22, 1985 [GB] United Kingdom ................ 8518422

[51] Int. Cl.$^4$ ................ C07D 499/00; A61K 31/425
[52] U.S. Cl. .................................. 514/192; 514/195; 540/310
[58] Field of Search ............... 540/310; 514/210, 192, 514/195

[56] References Cited

U.S. PATENT DOCUMENTS 4,485,110 11/1984 Osborne ................... 260/245.2 T

FOREIGN PATENT DOCUMENTS 0041768 12/1981 European Pat. Off. .
0120613 10/1984 European Pat. Off. .
0154132 9/1985 European Pat. Off. .

Primary Examiner—Nicholas S. Rizzo
Attorney, Agent, or Firm—Hopgood, Calimafde, Kalil, Blaustein & Judlowe

[57] ABSTRACT (5R) (Z)-6-(1-methyl,1,2,3-triazol-4-yl-methylene)-penem-3-carboxylic acid and its salts are provided in analytically pure crystalline form, and the salts in hydrated form, for example (5R) sodium (Z)-6-(1-methyl-1,2,3-triazol-4-yl-methylene)penem-3-carboxylate monohydrate.

29 Claims, 7 Drawing Sheets

HETEROCYCLIC-METHYLENE-PENEMS

This invention relates to novel β-lactam compounds and in particular to novel 6-(substituted methylene) penems which have β-lactamase inhibitory and antibacterial properties. The compounds are therefore useful in the treatment of antibacterial infections in humans or animals, either alone or in combination with other antibiotics.

European Patent Publication No. EP 0 041 768 A (Beecham; published Dec. 16, 1981; corresponding to U.S. Pat. No. 4 485 110) discloses 6-alkylidene-2-penems of the general formula (A):

in which
each of $R^a$ and $R^b$ denotes hydrogen or an optionally substituted hydrocarbon or heterocyclic group, and
$R^c$ denotes hydrogen or an organic group.

Those compounds possess antibacterial activity and also inhibit β-lactamases and have a synergistic effect in combination with other β-lactam antibiotics.

European Patent Publication No. EP 0 120 613 A (Beecham; published Oct. 3, 1984) discloses a sub-group of compounds within the general formula (A) which have better activity than other compounds of the general formula (A). That sub-group consists of compounds of the general formula (B):

in which
$R^c$ denotes hydrogen or an organic group;
one of $R^d$ and $R^e$ denotes hydrogen, and
the other of $R^d$ and $R^e$ denotes a group of the sub-formula (C):

in which
$R^f$ denotes a substituent group;
X denotes an oxygen atom, a sulphur atom or an =$NR^g$ group;
$R^g$ denotes hydrogen, hydrocarbon or a nitrogen-protecting group; and
n denotes 0, 1, 2 or 3.

European Patent Publication No. EP 0 154 132 A (Beecham; published Sept. 11, 1985 describes a further sub-group of compounds within the general formula (A), which exhibit improved β-lactamase inhibitory action and synergistic activity as compared with other compounds of that group. That sub-group consists of compounds of the general formula I:

and their pharmaceutically acceptable salts and in-vivo hydrolysable esters, in which
one of $R^1$ and $R^2$ denotes hydrogen,
the other of $R^1$ and $R^2$ denotes an unsubstituted or substituted five-membered hetero-aromatic ring bonded through a carbon atom thereof and having one hetero-atom selected from nitrogen, oxygen and sulphur and additionally having from one to three nitrogen atoms, and
$R_3$ denotes hydrogen or an organic group.

Such compounds are advantageously in the form of the 5R-isomer, that is to say in the form of structure IA:

One compound specifically described in European Patent Publication No. EP 0 154 132 A is the compound of the general formula IA in which $R^1$ denotes a 1-methyl-1,2,3-triazol-4-yl group and each of $R^2$ and $R^3$ denotes hydrogen, namely:
(5R) (Z)-6-(1-methyl-1,2,3-triazol-4-yl-methylene) penem-3-carboxylic acid;
as well as its pharmaceutically acceptable salts and in-vivo hydrolysable esters.

The compound is disclosed in the form of the freeze-dried sodium salts and also in the form of the crystalline free acid solvated with ethyl acetate (about 10-15%) (see Example 16(b) of No. EP 0 154 132 A, and also Preparation (1) below).

Further details of suitable esters and salts, and also details of methods of preparing the compounds and the manner of formulating them into pharmaceutical compositions and using them for therapeutic treatment, are given in European Patent Publication No. EP 0 154 132 A.

The biological activity of this compound may be demonstrated by the results in the following table. The table shows the antibacterial activity of the compound alone (designated '(5R)') against selected micro-organisms and, for comparison purposes, also gives the same data for amoxycillin; the data is given in the form of MIC values (minimum inhibitory concentration) in μg/ml. The table also shows the synergistic (β-lactamase inhibitory) activity of the compound when used in conjunction with amoxycillin against the same micro-organisms; the data is given in the form of the minimum inhibitory concentration of amoxycillin in μg/ml when used in conjunction with 5 μg/ml of the compound. In all cases, the compound was used in the form of its sodium salt.

TABLE

| Compound | Antibacterial Activity (MIC μg/ml) | | | |
|---|---|---|---|---|
| | P mirabilis C889 | E coli JT410 | C freundii Mantio | E aerogenes N1 |
| (5R) | 64 | 32 | 64 | 256 |
| Amoxycillin* | >512 | 256 | >512 | 512 |
| Amoxycillin plus (5R) | 2 | 1 | 2 | 2 |

*Typical MIC's from a number of tests

The present invention now provides (5R) (Z)-6-(1-methyl-1,2,3-triazol-4-yl-methylene)-penem-3-carboxylic acid (hereinafter referred to as 'the said penem') and salts thereof in analytically pure form, that is to say, in a purity of at least 98% by weight inclusive of any water of hydration.

The present invention also provides salts of the said penem in crystalline form (including microcrystalline form).

The present invention furthermore provides salts of the said penem in the form of a hydrate, more particularly in the form of a crystalline hydrate.

Advantageously, the salts of the said penem are pharmaceutically acceptable salts.

Suitable pharmaceutically acceptable salts include metal salts, e.g. aluminium salts, alkali metal salts (e.g. sodium or potassium salts), alkaline earth metal salts (e.g. calcium, barium or magnesium salts), ammonium salts, and substituted ammonium salts, for example those with lower alkylamines (e.g. triethylamine), hydroxy-lower alkylamines (e.g. 2-hydroxyethylamine), di(2-hydroxyethyl)amine or tri(2-hydroxyethyl)amine), cycloalkylamines (e.g. dicyclohexylamine), or with procaine, and also dibenzylamine, N,N-dibenzylethylenediamine, 1-ephenamine, N-ethylpiperidine, N-benzyl-β-phenethylamine, dehydroabietylamine, N,N'-bishydroabietylethylene-diamine, bases of the pyridine type (e.g. pyridine, collidine and quinoline), and other amines which have been or can be used to form salts with penicillins.

Alternatively, the said penem may be in the form of a salt which need not be pharmaceutically acceptable, but which may be useful as an intermediate in the preparation of a pharmaceutically acceptable product. Such a salt is, for example, a lithium salt.

Advantageously, the said penem is in the form of its sodium, potassium, lithium, calcium, magnesium or barium salt.

Thus, in a preferred embodiment, the present invention provides crystalline (5R) sodium (Z)-6-(1-methyl-1,2,3-triazol-4-ylmethylene)penem-3-carboxylate.

In another preferred embodiment, the present invention provides crystalline (5R) potassium (Z)-6-(1-methyl-1,2,3-triazol-4-ylmethylene)penem-3-carboxylate.

In yet another preferred embodiment, the present invention provides crystalline (5R) lithium (Z)-6-(1-methyl-1,2,3-triazol-4-ylmethylene)penem-3-carboxylate.

In yet another preferred embodiment, the present invention provides crystalline (5R) calcium (Z)-6-(1-methyl-1,2,3-triazol-4-ylmethylene)penem-3-carboxylate.

In yet another preferred embodiment, the present invention provides crystalline (5R) magnesium (Z)-6-(1-methyl-1,2,3-triazol-4-ylmethylene)penem-3-carboxylate.

In yet another preferred embodiment, the present invention provides crystalline (5R) barium (Z)-6-(1-methyl-1,2,3-triazol-4-ylmethylene)-penem-3-carboxylate.

In a further preferred embodiment, the present invention provides (5R) sodium (Z)-6-(1-methyl-1,2,3-triazol-4-yl-methylene)penem-3-carboxylate in the form of a hydrate, and particularly in the form of its monohydrate, more particularly its crystalline monohydrate, which is a stable form.

In a still further preferred embodiment, the present invention provides (5R) potassium (Z)-6-(1-methyl-1,2,3-triazol-4-yl-methylene)penem-3-carboxylate in the form of a hydrate, and particularly in the form of its monohydrate, more particularly its crystalline monohydrate, which is a stable form.

In a yet further preferred embodiment, the present invention provides (5R) lithium (Z)-6-(1-methyl-1,2,3-triazol-4-yl-methylene)penem-3-carboxylate in the form of a hydrate, and particularly in the form of its monohydrate, more particularly its crystalline monohydrate, which is a stable form.

In a yet further preferred embodiment, the present invention provides (5R) calcium (Z)-6-(1-methyl-1,2,3-triazol-4-yl-methylene)penem-3-carboxylate in the form of a hydrate, and particularly in the form of its tetrahydrate, more particularly its crystalline tetrahydrate, which is a stable form.

In a yet further preferred embodiment, the present invention provides (5R) magnesium (Z)-6-(1-methyl-1,2,3-triazol-4-yl-methylene)penem-3-carboxylate in the form of a hydrate, and particularly in the form of its dodecahydrate, more particularly its crystalline dodecahydrate, which is a stable form.

In a yet further preferred embodiment, the present invention provides (5R) barium (Z)-6-(1-methyl-1,2,3-triazol-4-yl-methylene)penem-3-carboxylate in the form of a hydrate, and particularly in the form of a crystalline hydrate, which is a stable form.

All such crystalline and/or hydrated salts are advantageously provided in analytically pure form.

According to yet another preferred embodiment, the present invention provides crystalline (5R) (Z)-6-(1-methyl-1,2,3-triazol-4-yl-methylene)penem-3-carboxylic acid free of solvation by ethyl acetate.

According to another preferred embodiment, the present invention provides crystalline (5R) (Z)-6-(1-methyl-1,2,3-triazol-4-yl-methylene)-penem-3-carboxylic acid, free of solvation by an organic solvent.

According to another preferred embodiment, the present invention provides crystalline (5R) (Z)-6-(1-methyl-1,2,3-triazol-4-yl-methylene)-penem-3-carboxylic acid in analytically pure form.

The present invention also provides a process for the preparation of (5R) (Z)-6-(1-methyl-1,2,3-triazol-4-yl-methylene)-penem-3-carboxylic acid or a salt thereof, which comprises crystallising the said acid or salt from an aqueous medium.

The present invention furthermore provides a process for the purification of (5R) (Z)-6-(1-methyl-1,2,3-triazol-4-yl-methylene)-penem-3-carboxylic acid or a salt thereof, which comprises crystallising the said acid or salt from an aqueous medium.

Such crystallisation enables the obtention of an analytically pure product. It also enables the obtention of the salts in crystalline and/or hydrated form. Furthermore, it enables the obtention of the crystalline free acid form of the penem free of solvation by ethyl acetate or another organic solvent.

Crystallisation of a salt of the said penem may be effected by conventional techniques. Crystallisation may, for example, conveniently be effected by slurrying or wetting a sample thereof with an aqueous medium, e.g. water, at ambient temperature or with cooling if necessary to initiate crystallisation. Alternatively, crystallisation may be effected from a solution of the salt in an aqueous medium, by cooling, by volume-reduction (e.g. evaporation) of, or by seeding, the solution, or by a combination of two or more such methods.

The aqueous medium used for slurrying, wetting and/or dissolving the salt, may be water or may also contain an organic diluent. Suitable organic diluents include, for example, acetone, ethanol, acetonitrile, acetone/diethyl ether mixtures, and other inert water-miscible solvents. The ratio of water:organic diluent may suitably be from 500:1 to 1:500, for example from 100:1 to 1:100, from 10:1 to 1:10, or from 2:1 to 1:2.

The sample of the salt used for the crystallisation may conveniently be an amorphous sample thereof, for example a freeze-dried sample thereof, produced by the methods described in the above-mentioned European and U.S. patent documents, such as by the methods more particularly described in the Preparations and Examples below.

The sample of the salt used for the crystallisation may suitably have first been subjected to column chromatography in order to purify it at least partially. Suitable column packing materials for such purification include, for example, silica, cellulose, Bio-Gel P2 (from Bio-Rad Laboratories, Richmond, Calif., U.S.A.), Diaion HP20SS, Sepabeads SP207 (both from Mitsubishi Chemical Corp.), Fractogel SK HW-40(S), Amberlite XAD-2 and XAD-4 (all from E. Merck, Darmstadt, Germany), Duolite S861 and S862 (from Rohm and Haas), and Kastel S112; ('Bio-Gel', 'Diaion', 'Sepabeads', 'Fractogel' 'Amberlite', 'Duolite', and 'Kastel' are Trade Marks).

The sample of the salt used for the crystallisation may, according to another embodiment of the process according to the invention, be prepared in situ, from the penem free acid or another salt thereof by conventional techniques.

One suitable conventional technique for such in situ preparation of the salt involves neutralisation of the penem free acid by a base. Suitable bases for effecting such neutralisation include, for example, hydroxides, bicarbonates, carbonates, acetates, formates, and ethylhexanoates of the desired cation. In the case of the alkali metal and barium salts, it is generally convenient to use, for example, the corresponding hydroxide or another water-soluble salt, whereas in the case of the calcium and magnesium salts it is generally convenient to use, for example, the corresponding ethylhexanoate or another organic-soluble salt.

Suitable conventional techniques for in situ preparation of the desired salt from another salt of the penem involve exchange of the cations of the salts. This may, for example, be effected by so-called 'double decomposition' in which the initial penem salt is reacted with an approximately equimolar amount of a salt containing the desired cation. Alternatively, it may, for example be effected by so-called 'salting out', in which the initial penem salt is reacted with a large excess of another salt, for example, a halide of the desired cation, so as to cause the desired penem salt to precipitate out. A further method involves passing the initial penem salt through an ion-exchange resin, containing the desired cation bound to the resin, so that the desired penem salt elutes from the ion-exchange column.

Such in situ preparation of the salt may, where appropriate, be carried out directly in an aqueous medium. In some cases, however, for example in the cases of the calcium and magnesium salts, it may be convenient initially to prepare the desired salt in an organic solvent and subsequently to transfer it to an aqueous medium for the crystallisation. The organic solvent used for that purpose may or may not be water-miscible, and suitable organic solvents include, for example, methyl isobutyl ketone and acetone. The transfer of the salt to the aqueous medium may, for example, be effected by freeze-drying followed by further processing as discussed previously. In the case of a water-immiscible organic solvent, the transfer may, for example, be effected by two-phase extraction or, in the case of a water-miscible organic solvent, it may, for example, be effected simply by the addition of water to the aqueous solution.

Crystallistion of the penem free acid may suitably be effected by producing the penem free acid in situ in an aqueous medium. The penem free acid is only sparingly soluble in water and immediately crystallises from the aqueous medium. This may conveniently be effected by acidifying a solution or slurry of a salt of the penem, for example the sodium salt, in an aqueous medium. In this case, the aqueous medium is preferably free, or substantially free, of organic solvent (i.e. the aqueous medium is preferably water) in order to avoid any solvation of the penem free acid.

It has been found that crystallisation of the penem free acid in this way provides a particularly good, simple and convenient way of purifying the penem or salt and, in particular, removing certain water-soluble impurities, which remain dissolved in the aqueous medium when the free acid precipitates out.

Thus, according to a particularly preferred embodiment, the present invention provides a process for the purification of (5R) (Z)-6-(1-methyl-1,2,3-triazol-4-ylmethylene)-penem-3-carboxylic acid or a salt thereof, which comprises acidifying a salt of the said penem in an aqueous medium, and isolating the resulting precipitated penem free acid and, if desired, subsequently converting the penem free acid to a salt thereof.

The crystallised penem free acid or salt obtained according to any of the above techniques may suitably be filtered off and washed with, for example, water (preferably ice-cold water) and/or an organic diluent, for example acetone or diethyl ether, and may then be allowed to dry, suitably at ambient temperature and pressure.

If desired, crystallisation may be repeated in a similar manner. On crystallisation by the methods described above, the salts of the said penem may be produced in the form of hydrates. Furthermore, the said penem and the salts may be produced in analytically pure form.

As indicated previously, the compounds according to the invention have β-lactamase inhibitory activity and are useful in the treatment of bacterial infections.

Accordingly, according to a further aspect, the present invention provides a pharmaceutical composition comprising a compound according to the invention in admixture or conjunction with a pharmaceutically acceptable carrier. The composition may also comprise a penicillin, cephalosporin or other β-lactam antibiotic.

Details of formulating such compositions and using the compound according to the invention are given in our above-mentioned No. EP 0 154 132 A, the contents of which are incorporated herein by reference.

The following examples illustrate the present invention. The preparation of the starting material for the examples is described in Preparations (a) to (1). The accompanying FIGS. 1 to 7 show infra-red spectra of the products produced in Examples 3 to 9, respectively. The spectrum of FIG. 1 was run on a Perkin-Elmer 197 machine (speed: slow); the spectra of FIGS. 2 to 7 were run on a Perkin-Elmer 983 machine (scan mode: 4; noise filter: 1; resolution: 3). All spectra were run using Nujol mulls between KBr plates, against air as the reference. In the Figures, wavenumber (400–4000 cm$^{-1}$) is shown on the horizontal axis and transmittance (0–100%) is shown on the vertical axis.

Preparation (a)

Ethyl 1-methyl-1,2,3-triazole-4-carboxylate

A solution of ethyl propiolate (16.2 ml) in hexane (50 ml) was added, dropwise over 30 minutes with stirring, to ice-salt bath cooled methyl azide [prepared by addition of dimethyl sulphate (18.9 ml) to a stirred solution of sodium azide (13 g) in 1N sodium hydroxide (100 ml) at 70° C. according to the method of O. Dimroth, *Chem. Ber.*, 1905, 38, 1573]. The stirred mixture was allowed to attain room temperature during 2 hours and stood for a further 20 hours. The hexane liquors were decanted from the crystalline product which was washed with hexane (3×10 ml) and dried under vacuum to give the title ester (1) (3.39 g), m.p. 90°–91° C. (colourless needles), $\nu_{max}$ (CHCl$_3$) 1720 cm$^{-1}$; δppm (CDCl$_3$) 1.40 (3H, t, J7Hz), 4.20 (3H, s), 4.44 (2H, q, J7Hz), 8.18 (1H, s). (Found: C, 46.4; H, 5.8; N, 27.0. C$_6$H$_9$N$_3$O$_2$ requires C, 46.4; H, 5.8; N, 27.1%).

The combined hexane liquors and washings were kept at room temperature for a further 9 days when a second crop of the title ester (1) (6.98 g), mp 90°–91° C. was obtained after decanting, washing with hexane (3×20 ml) and drying under vacuum.

Preparation (b)

(3S, 4R) 3-Bromo-1-t-butyldimethylsilyl-4-tritylthioazetidin-2-one

A solution of triethylamine (116 mg) in dry dimethylformamide (1 ml) was added, dropwise over 1.5 minutes, to a stirred solution of (3S, 4R) 3-bromo-4-tritylthi-oazetidin-2-one (424 mg) (A. Martel et al., *Can. J. Chem.*, 1983, 61, 1899) and t-butyldimethylchorosilane (188 mg) in dry dimethylformamide (4 ml) at ice-bath temperature. The mixture was stirred at room temperature overnight, diluted with ethyl acetate (30 ml), and washed with 5% citric acid (2 ml), brine (2 ml), saturated sodium bicarbonate solution (2 ml), and brine (3×2 ml). The dried (MgSO$_4$) organic layer was evaporated and the residue chromatographed on silica gel eluting with ethyl acetate/hexane mixtures to give the title azetidinone (2) (471 mg), a solid, m.p. 115°–116° C. (rods ex ethyl acetate/hexane); [α]D$^{22}$−31.8° (c 1 in CHCl$_3$); $\nu_{max}$ (CHCl$_3$) 1755 cm$^{-1}$; δppm (CDCl$_3$) 0.90 (9H, s), 4.25 (1H, s), 4.30 (1H, s), 7.10–7.50 (15H, m), both Me$_3$Si signals were obscured by TMS. (Found: C, 62.6; H, 5.9; N, 2.6; S, 5.9; Br, 14.7. C$_{28}$H$_{32}$NBrOSSi requires C, 62.4; H, 6.0; N, 2.6; S, 6.0; Br, 14.8%).

Preparation (c)

(3S, 4R) 1-t-Butyldimethysilyl-3-(1-methyl-1,2,3-triazol-4-ylcarbonyl)-4-tritylthioazetidin-2-one A solution of n-butyl lithium (1.68M in hexane, 0.595 ml) was added to a stirred solution of the azetidinone (2) (538 mg) from Preparation (b) in dry THF (10 ml) at −76° C. under dry argon. After 10 minutes at −76° C. the stirred mixture was treated, in one portion, with a solution of the triazole ester (1) (155 mg) from Preparation (a) in dry THF (3 ml). After 10 minutes at −76° C. the stirred mixture was treated with saturated ammonium chloride solution (3 ml) and allowed to attain room temperature. The mixture was diluted with ethyl acetate (30 ml) and was washed with brine (3×5 ml). The dried (MgSO$_4$) organic layer was evaporated and the residue chromatographed on silica gel eluting with ethyl acetate/hexane mixtures to give the title ketone (3) (387 mg) as an amorphous solid, [α]D$^{22}$ 58.6° (c 1 in CHCl$_3$); $\nu_{max}$(CHCl$_3$) 1750, 1680 cm$^{-1}$; δppm (CDCl$_3$) 0.92 (9H, s), 4.06 (3H, s), 4.70 (1H, d, J2Hz), 4.95 (1H, d, J2Hz), 6.9–7.5 (15H, m), 7.83 (1H, s), both Me$_3$Si signals were obscured by TMS.

Preparation (d)

(3S,4R) 1-t-Butyldimethylsilyl-3-[hydroxy(1-methyl-1,2,3-triazol-4-yl)methyl]-4-tritylthioazetidin-2-one A solution of the ketone (3) (300 mg) from Preparation (c) in THF (3 ml) and ethanol (3 ml) at 5° C. was treated, portionwise, with sodium borohydride (40 mg). The mixture was stirred at room temperature for one hour, then diluted with ethyl acetate and acidified with 5% citric acid solution. The organic layer was separated, washed with brine, saturated sodium bicarbonate solution and brine, then dried and (MgSO$_4$) evaporated. The residue was chromatographed on silica eluting with ethyl acetate/hexane mixtures to give two fraction. The less polar fraction contained an isomer (Isomer A) of the title trans-azetidinone (4) (67 mg) m.p. 195°–197° C. (needles ex ethyl acetate/hexane); [α]D$^{22}$+69.00 (c 1 in CHCl$_3$); $\nu_{max}$(CHCl$_3$) 3600–3100, 1735 cm$^{-1}$; δppm (CDCl$_3$) 0.93 (9H, s), 1.84 (1H, brs, exch. D$_2$O), 3.29–3.38 (1H, m), 3.88 (1H, d, J2Hz), 3.95 (3H, s), 4.51 (1H, d, J2Hz), 7.10–7.50 (15H, m), 7.82 (1H, s), both Me$_3$Si signals were obscured by TMS. (Found: C, 67.8; H, 6.7; N, 9.6; S, 5.6. C$_{32}$H$_{38}$N$_4$O$_2$SSi requires C, 67.3; H, 6.7; N, 9.8; S, 5.6%). The more polar fraction contained the other isomer (Isomer B) of the trans azetidinone (4) (167 mg) m.p. 128°–130° C. (plates ex ethyl acetate/hexane); [α]D$^{22}$−2.5° (c 1 in CHCl$_3$); $\nu_{max}$ (CHCl$_3$) 3600–3100, 1730 cm$^{-1}$; δppm (CDCl$_3$) 0.78 (9H, s), 2.31 (1H, brs, exch. D$_2$O), 3.60 (1H, dd, J6 and 2Hz), 3.92 (3H, s),4.11 (1H, d, J6Hz), 4.43 (1H, d, J2Hz), 7.10–7.60 (16H, m), both Me$_3$Si signals were obscured by TMS. (Found: C, 66.8; H, 6.9; N, 9.8; S, 5.4. C$_{32}$H$_{38}$N$_4$O$_2$SSi requires C, 67.3; H 6.7; N, 9.8; S, 5.6%).

Preparation (e)

(3S, 4R) 3-[Hydroxy(1-methyl-1,2,3-triazol-4-yl)methyl]tritylthioazetidin-2-one A solution of anhydrous potassium fluoride (339 mg) in methanol (10 ml) was added to a stirred solution of the alcohol (4) (Isomer B) (3.03 g) from Preparation (d) in methanol (50 ml) and dichloromethane (10 ml) at −20° C. After 1.25 hours the mixture was evaporated to low volume, diluted with ethyl acetate (150 ml) and washed with brine, then dried (MgSO$_4$) and evaporated. The crude product was triturated with dry ether to give the title azetidinone (5) (2.15 g) as a solid, m.p. 196°–197° C. (nuggets ex ethyl acetate/hexane); $[\alpha]D^{22} -124.7°$ (c 1 in CHCl$_3$); $\nu_{max}$ (CHCl$_3$) 3600–3100, 1760 cm$^{-1}$; $\delta$ppm (CDCl$_3$) 3.64 (1H, dd, J5 and 2Hz), 3.65–3.95 (1H, br. signal, exch. D$_2$O), 4.16 (3H, s), 4.33 (1H, s), 4.60 (1H, d, J2Hz), 5.26 (1H, slightly broadened d, J5Hz, sharpens on exch. D$_2$O), 7.19–7.42 (15H, m), 7.63 (1H, s). (Found: C, 68.3; H, 5.3; N, 12.4; S, 7.0. C$_{26}$H$_{24}$N$_4$O$_2$S requires C, 68.4; H 5.3; N, 12.3; S, 7.0%).

Preparation (f)

(3S, 4R) 3-[Acetoxy (1-methyl-1,2,3-triazol-4-yl) methyl]-4-tritylthioazetidin-2-one A solution of the azetidinone (5) (2.10 g) from Preparation (e) in dry dichloromethane (40 ml) at 5° C. was sequentially treated with triethylamine (0.77 ml), 4-dimethylaminopyridine (56 mg) and acetic anhydride (0.52 ml). After 30 minutes the mixture was washed with 5% citric acid solution, brine, sodium bicarbonate solution and brine, then dried (MgSO$_4$) and evaporated. The residue was chromatographed on silica eluting with ethyl acetate/hexane mixtures to give the title acetate (6) (2.29 g) as a solid, m.p. 111°–113° C. (nuggets ex benzene/hexane); $[\alpha]D^{21} -97.0$ (c 1 in CHCl$_3$); $\nu_{max}$ (CHCl$_3$) 3390, 1770 cm$^{-1}$; $\delta_{ppm}$ (CDCl$_3$) 2.11 (3H, s), 3.84 (1H, ddd, J6.5, 2.6 and 1.1Hz); 4.11 (3H, s), 4.17 (1H, brs), 4.70 (1H, d, J2.6Hz), 6.17 (1H, d, J6.5Hz), 7.22–7.58 (16H+approximately 1 mole benzene, m). (Found; C, 70.8; H, 5.7; N, 9.6; S, 5.5. C$_{28}$H$_{26}$N$_4$S.C$_6$H$_6$ requires C, 70.8; H, 5.6; N, 9.7, S, 5.6%).

Preparation (g)

(3S, 4R) 3-[Acetoxy (1-methyl-1,2,3-triazol-4-yl) methyl]-1-(1-p-nitrobenzyloxycarbonyl-1-triphenyl phosphoranylidenemethyl)-4-tritylthioazetidin-2-one The acetate (6) (2.22 g) from Preparation (f) and p-nitrobenzylglyoxylate monohydrate (1.11 g) were heated in refluxing benzene (50 ml) with provision for azetropic removal of water (Dean and Stark apparatus containing molecular sieves 4A) for one hour. The mixture was cooled to room temperature and treated with triethylamine (45 mg). After 30 minutes the mixture was evaporated to give the crude hydroxyesters (7) as an amorphous solid; $\nu_{max}$ (CHCl$_3$) 3600–3100, 1770 br, cm$^{-1}$. A solution of the crude hydroxyesters (7) in dry THF (30 ml) was cooled to −10° C. and treated with 2,6-lutidine (0.78 ml) and thionyl chloride (0.49 ml). After 10 minutes the mixture was filtered and evaporated. The residue was re-evaporated from toluene (2x) to give the crude chloroester (8) as an amorphous solid; $\nu_{max}$(CHCl$_3$) 1780 cm$^{-1}$. The crude chloroester (8) and triphenylphosphine (4.67 g) were stirred in dry dioxan (5 ml) for 10 minutes. The resulting solution was evaporated to approximately half volume and treated with 2,6-lutidine (0.62 ml). The mixture was stirred at 40° C. for 20 hours, then diluted with ethyl acetate (100 ml) and washed with 5% citric acid solution, brine, saturated sodium bicarbonate solution, and brine then dried (MgSO$_4$) and evaporated. The residue was chromatographed on silica eluting ethyl acetate/hexane mixtures to afford the title phosphorane (9) (3.66 g), $[\alpha]D^{20} -33.0°$ (c 1 in CHCl$_3$); $\nu_{max}$(CHCl$_3$) 1750, 1620, 1605 sh cm$^{-1}$.

Preparation (h)

(3S, 4R) Silver 3-[Acetoxy (1-methyl-1,2,3-triazol-4-yl) methyl]-1-(1-p-nitrobenzyloxycarbonyl-1-triphenyl phosphorylidenemethyl)-azetidin-2-one-4-thiolate.

Silver nitrate (8.7 ml of a 0.15M solution in methanol) was added to a stirred mixture of the phosphorane (9) (951 mg) from Preparation (g) and pyridine (0.015 ml) in methanol (10 ml) and dichloromethane (1 ml). After stirring at room temperature for 30 minutes the mixture was evaporated. The residual gum was re-evaporated from dry dichloromethane (5 ml) and dried under vacuum to give the crude title silver salt (10) as an amorphous solid. The material was of sufficient purity for further synthetic elaboration.

Preparation (i)

(5R, 6S) p-Nitrobenzyl 6-[acetoxy(1-methyl-1,2,3-triazol-4-yl)methyl]penem-3-carboxylate A stirred solution of the crude silver salt (10) from Preparation (h) in dichloromethane (20 ml) at 5° C. under argon was treated with 4-dimethylaminopyridine (122 mg) and formic acetic anhydride (0.8 ml). The reaction mixture was removed from the ice-bath and immediately treated with triethylammonium chloride (1.37 g). After vigorous stirring for 10 mintues the mixture was diluted with ethyl acetate (30 ml) and filtered through Kieselguhr, washing pad with ethyl acetate. The filtrate was washed with 5% citric acid solution, brine, saturated sodium bicarbonate solution and brine. The dried (MgSO$_4$) organic layer was heated under argon for 45 minutes at 40° C., then evaporated and the residue was chromatographed on silica eluting with dichloromethane/ethyl acetate mixtures to provide the title penem (11) (378 mg) as a solid, mp. 151°–153° C. (hexagonal plates ex ethyl acetate/hexane); $[\alpha]D^{20} +24.0°$ (c 1 in CHCl$_3$); $\lambda_{max}$ (2% CHCl$_3$in EtOH) 262 (em 13380) and 316 nm (8889); $\nu_{max}$(CHCl$_3$) 1795, 1740 sh, 1720 cm$^{-1}$; $\delta$ppm (CDCl$_3$) 2.09 (3H, s), 4.09 (3H, s), 4.56 (1H, ddd, J3.4, 2.2 and 1.0Hz), 5.25 and 5.43 (2H, ABq, J13.6 Hz), 6.20 (1H, d, J3.4 Hz), 6.23 (1H, d, J2.2 Hz), 7.36 (1H, d, J1.0 Hz), 7.60 (2H, d, J8.7 Hz), 7.67 (1H, s), 8.23 (2H, d, J8.7 Hz). (Found: C,49.7; H, 3.7; N, 15.2; S, 6.9. C$_{19}$H$_{17}$N$_5$O$_7$S requires C,49.7; H, 3.7; N, 15.3; S, 7.0%).

Preparation (j)

(5R) p-Nitrobenzyl 6-(1-methyl-1,2,3-triazol-4-yl methylene)penem-3-carboxylate

A solution of the penem (11) (315 mg) from Preparation (i) in dry dichloromethane (5 ml) at −40° C. under argon was treated dropwise with a solution of 1,8-diazabicyclo[5.4.0]undec-7-ene (157 mg) in dichloromethane (0.5 ml). After 10 minutes the mixture was diluted with dichloromethane (20 ml) and washed with 5% citric acid solution, brine, saturated sodium bicarbonate solution and brine, then dried (MgSO$_4$) and evaporated. The residue was chromatographed on silica eluting with dichloromethane/ethyl acetate mixtures to give two fractions. The less polar fraction contained the (Z)-isomer (12) (243 mg) of the title penem, a solid, m.p. 174°–175° C. (microcrystalline solid dichloromethane/hexane); $[\alpha]D^{20} +343.2°$ (c 1 in CHCl$_3$); $\nu_{max}$ (2%

CHCl₃ in EtOH) 282 nm ($\epsilon_m$ 27183); $\nu_{max}$ (CHCl₃) 1780, 1715 cm$^{-1}$; $\delta$ppm (CDCl₃) 4.16 (3H, s), 5.29 and 5.46 (2H, ABq, J13.6 Hz), 6.68 (1H, d, J1.0 Hz), 7.06 (1H, d, J1.0 Hz), 7.39 (1H, s), 7.62 (2H, d, J8.9 Hz), 7.73 (1H, s), 8.24 (2H, d, J8.9 Hz), a singlet at 5.30 ppm indicated the presence of dichloromethane. (Found: C, 48.7; H, 3.2; N, 16.4; S, 7.5; Cl, 5.1%). The more polar fraction contained the (E)-isomer (13) (7 mg) of the title penem, a solid, $\nu_{max}$ (Nujol Mull) 1750, 1710, 1685 cm$^{-1}$; $\delta$ppm (CDCl₃) 4.17 (3H, s), 5.31 and 5.47 (2H, ABq, J13.6 Hz), 6.49 (1H, s), 6.95 (1H, s), 7.46 (1H, s), 7.62 (2H, d, J8.7 Hz), 8.26 (2H, d, J8.7 Hz), 8.74 (1H, s).

Preparation (k)

(5R) Sodium (Z)-6-(1-methyl-1,2,3-triazol-4-yl methylene)penem-3-carboxylate

The (Z)-penem ester (12) (200 mg) from Preparation (j) was dissolved in a mixture of dioxan (16 ml) and water (4 ml) and hydrogenated over 5% palladium/-charcoal catalyst (300 mg) at S.T.P. for 45 minutes. A 1% sodium bicarbonate solution (4.21 ml) was added and the mixture was filtered through Kieselguhr, the residue being washed with a little aqueous dioxan. The combined filtrates were evaporated and the residue chromatographed on Bio-Gel P2 eluting with water. The appropriate fractions (by u.v., t.l.c. or h.p.l.c.) were freeze-dried to give the title sodium salt (14) (81 mg) as a yellow freeze-dried solid, $[\alpha]D^{18}+400°$; $\nu_{max}$ (H₂O) 282 nm ($\epsilon_m$ 18459) and 354 (1589); $\nu_{max}$ (KBr) 3700–2750, 1760, 1680, 1600, 1555 cm$^{-1}$; $\delta$ (D₂O) 4.10 (3H, s), 6.57 (1H, s), 7.02 (1H, s), 7.17 (1H, s), 8.13 (1H, s).

Preparation (l)

Crystalline (5R) (Z)-6-(1-methyl-1,2,3-triazol-4-ylmethylene)-penem-3-carboxylic acid The penem sodium salt (14) (14 mg) from Preparation (k) was partitioned between ethyl acetate (10 ml) and water (2 ml) and cooled in an ice bath. The pH of the vigorously stirred mixture was adjusted to 3.5 using 1% citric acid. The organic layer was separated and washed with water (3×1 ml). The dried (MgSO₄) organic layer was evaporated to give a crude solid. The crude solid was redissolved in ethyl acetate (20 ml) and filtered through Kieselguhr. The filtrate was evaporated to low volume (approximately 1 ml) and diluted with a little hexane to give the free acid of the title penem (15) as yellow clusters of prisms, slow decomposition >150° C. finally melting at approximately 230° C.; $\nu_{max}$ (Nujol) 3400–2800, 1775, 1720, 1700 br. cm$^{-1}$; $\delta$ppm [(CD₃)₂SO) 4.10 (3H,s), 6.64 (1H, d, J 0.7 Hz), 7.32 (1H, d, J 0.7 Hz), 7.57 (1H,s), 8.39 (1H,s), 12.87 br (1H,s), other signals indicated the presence of 10–15% ethyl acetate.

EXAMPLE 1

Crystalline sodium (5R)(Z)-6-(1-methyl-1,2,3-triazol-4-ylmethylene)-penem-3-carboxylate The freeze-dried sodium salt (14) (20 mg) from Preparation (k) was slurried with water (0.2 ml) at ambient temperature whereupon crystallisation occurred spontaneously to give the crystalline sodium salt (16).

EXAMPLE 2

Sodium (5R)(Z)-6-(1-methyl-1,2,3-triazol-4-ylmethylene) penem-3-carboxylate monohydrate Freeze-dried sodium salt (14) (550 mg) from Preparation (k), purified by passage through Diaion HP20SS using water as eluant, was wetted with water (3.0 ml), seeded and cooled in ice and water for 30 minutes. The crystalline solid was collected by filtration, washed with ice-cold water (<1 ml), acetone and ether and allowed to air-dry to constant weight to provide the title sodium salt monohydrate (17a) (400 mg); (Found: C, 39.54; H, 2.85; N, 18.43; S, 10.55. C₁₀H₉N₄O₄SNa requires C, 39.47; H, 2.96; N, 18.42; S, 10.53%).

EXAMPLE 3

Figure 1:
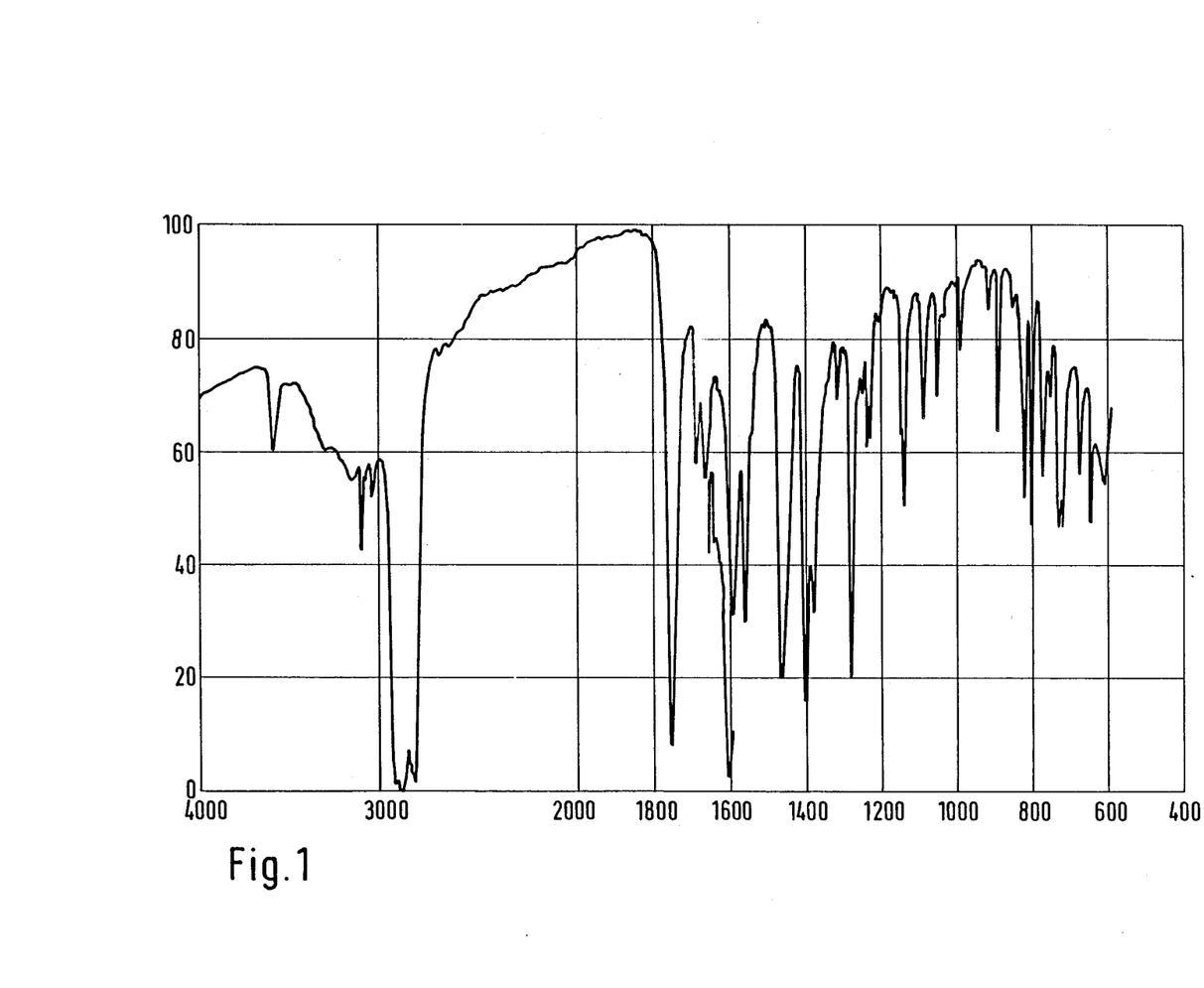

Sodium (5R)(Z)-6-(1-methyl-1,2,3-triazol-4-ylmethylene) penem-3-carboxylate monohydrate Water (5.5 ml) was added to the crystalline material (390 mg) obtained in Example 2 and the suspension was warmed at 55° C. until all the material was in solution. The solution was filtered and then allowed to cool. A small quantity of seed crystals was added, and then the solution was cooled in ice-water. After one hour the crystalline solid was collected by filtration, washed with ice-cold water (approx. 0.5 ml), acetone and finally ether, then air-dried to constant weight to provide the title sodium salt monohydrate (17b) (150 mg) as plates; $[\alpha]_D^{20}$ (c 1.0 in water) +512.5°; $\nu_{max}$ (H₂O) 282 nm ($\epsilon_m$ 23720), 365 (1880); $\nu_{max}$ (KBr) 3605, 1749, 1688, 1663, 1589, 1558, 1397, 1274 cm$^{-1}$; $\delta$ (D₂O) 4.11 (3H, s), 6.57 (1H, s), 7.02 (1H, s), 7.17 (1H, s), 8.14 (1H, s); (Found: C, 39.62; H, 2.84; N, 18.33; S, 10.48. C₁₀H₉N₄O₄SNa requires C, 39.47; H, 2.96; N, 18.42; S, 10.53%). The infrared spectrum of the product is shown in the accompanying FIG. 1. The mother liquors were diluted further with acetone and then cooled in ice-water. The crystalline solid was collected by filtration, washed with acetone and ether, then air-dried to constant weight to provide a further quantity (220 mg) of the title compound.

EXAMPLE 4

Figure 2:
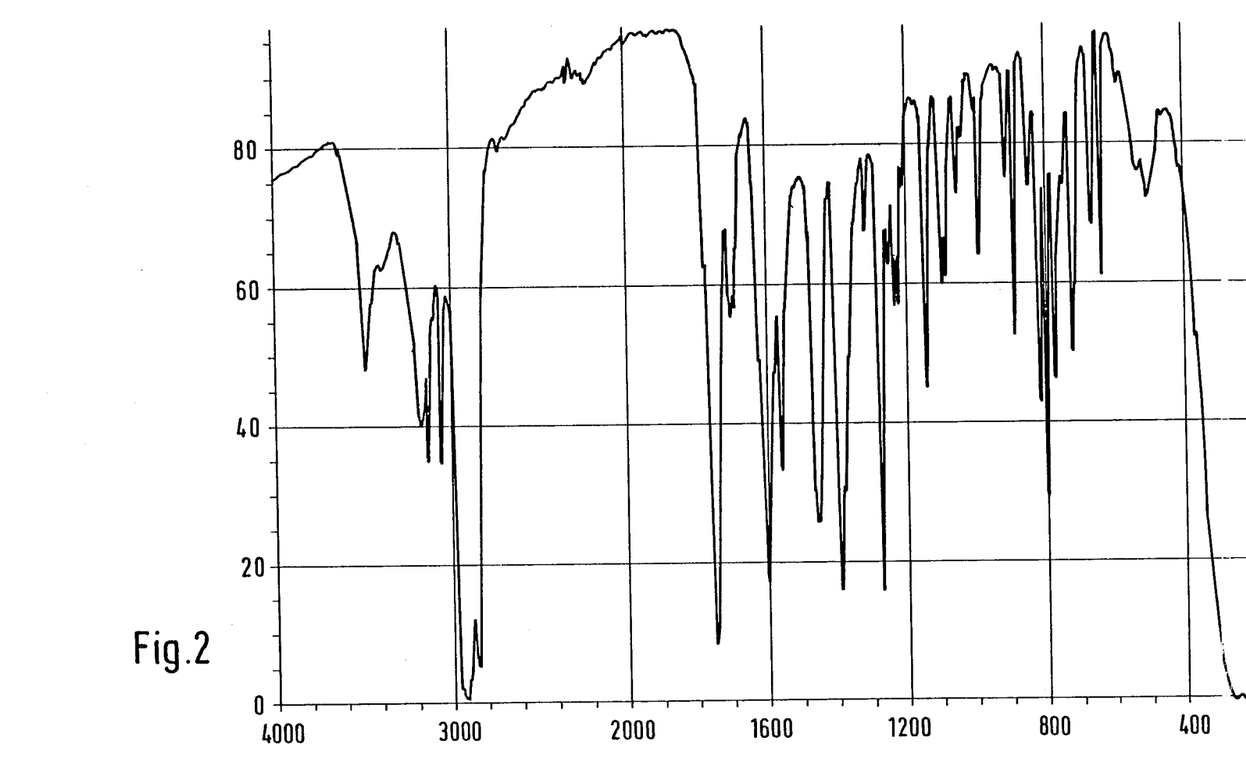

Potassium (5R) (Z)-6-(1-methyl-1,2,3-triazol-4-ylmethylene)penem-3-carboxylate monohydrate A stirred solution of the sodium salt monohydrate (17a) (500 mg) in water (20 ml) was treated dropwise with 1N sulphuric acid solution until a pH of 2 was obtained. The resulting crystalline yellow solid (see Example 5) was filtered onto a glass-fibre filter paper and washed well with water. The solid and filter paper were then added to water (50 ml) and the mixture was vigorously stirred. The pH was carefully adjusted to 7 with 0.1M potassium hydroxide solution.(During addition of the base a pH of 7.5 was not exceeded at any time.) The solution was then filtered and evaporated to low volume (approx. 10 ml) whereupon crystallization occurred. The crystalline solid was collected by filtration, washed with ice-cold water (0.5 ml), acetone and ether and allowed to air-dry to constant weight to provide the title potassium salt monohydrate (18)(293 mg) as needles; $[\alpha]_D^{20}$ (c 1 in water) +492.3°; $\nu_{max}$ (H₂O) 282 nm ($\epsilon_m$ 24,900), 368 (1,800); $\nu_{max}$ (nujol) 3489, 1753, 1703, 1600, 1561 cm$^{-1}$; δ(D$_2$O) 4.07 (3H, s), 6.54 (1H, d, J 0.8 Hz), 6.99 (1H, s), 7.14 (1H, d, J 0.8 Hz), 8.10 (1H, s); (Found; C, 37.65; H, 2.79; N, 17.45; S, 10.18. C$_{10}$H$_7$N$_4$O$_3$SK.H$_2$O requires C, 37.49; H, 2.83; N, 17.48; S, 10.01%). The infra-red spectrum of the product is shown in the accompanying FIG. 2.

EXAMPLE 5

Figure 3:
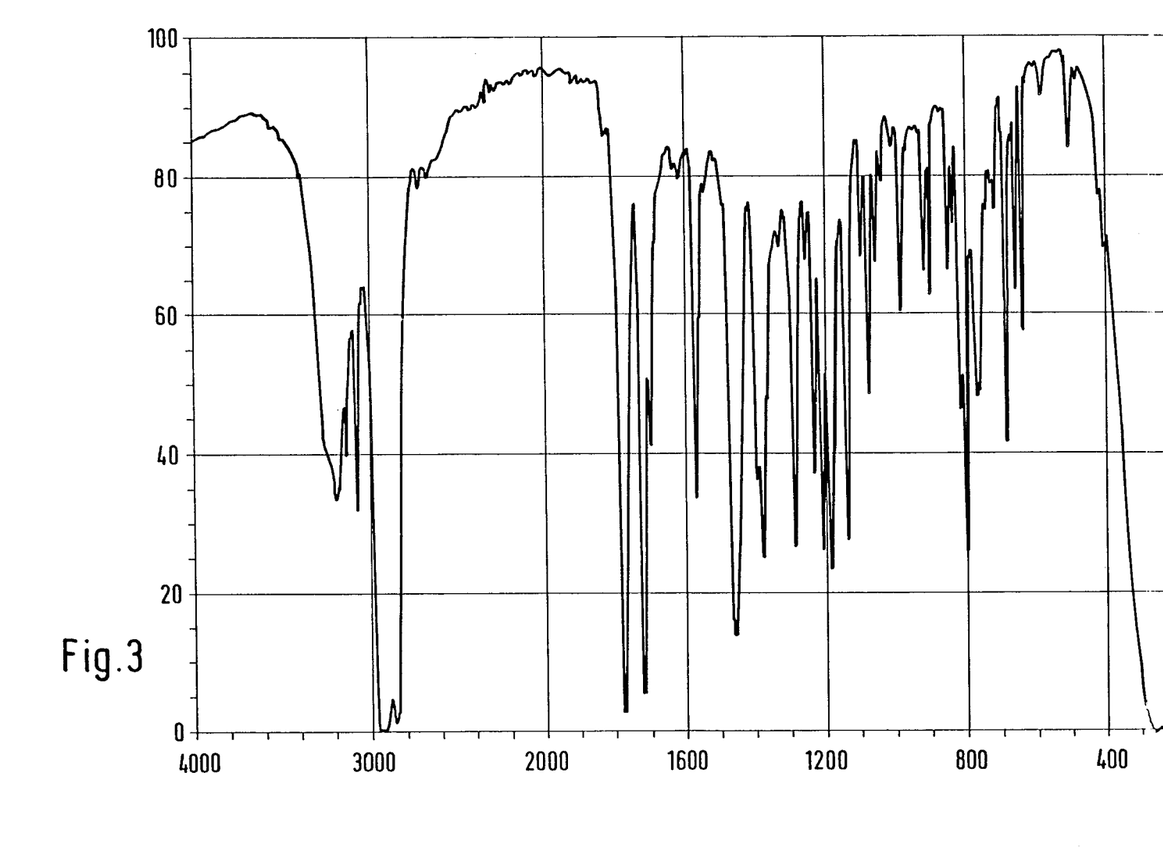

Crystalline (5R) (Z)-6-(1-Methyl-1,2,3-triazol-4-ylmethylene)penem-3-carboxylic acid A freeze-dried mixture of sodium and potassium salts of the title compound (assayed as 84.4% of the title free acid) (100 mg) was dissolved in water (15 ml) and treated dropwise with 1N sulphuric acid solution until a pH of 2 was obtained. The resulting crystalline yellow solid was collected by filtration, washed well with water, then acetone (<0.25 ml), and ether and dried to provide the title free acid (19)(78 mg) as needles; $\nu_{max}$ (nujol) 3182 (br), 1775, 1720, 1700, 1614 cm$^{-1}$; δ(d$_7$-DMF) 4.19 (3H, s), 6.68 (1H, s), 7.32 (1H, s), 7.58 (1H, s), 8.46 (1H, s). (Found C, 45.53; H, 2.96; N, 21.14; S, 12.11. C$_{10}$H$_8$N$_4$O$_3$S requires C, 45.45; H, 3.03; N, 21.21; S, 12.12%). The analytical data shows the crystalline free acid to be analytically pure and to be free of solvation by any organic solvent. Its infra-red spectrum is shown in the accompanying FIG. 3.

This material may be slurried with water and treated dropwise with a suitable base until a pH of 7 is achieved. The resulting aqueous solution of the salt of the title penem can then be crystallized either by freeze-drying and then wetting with water or by reducing the volume by evaporation.

EXAMPLE 6

Figure 4:
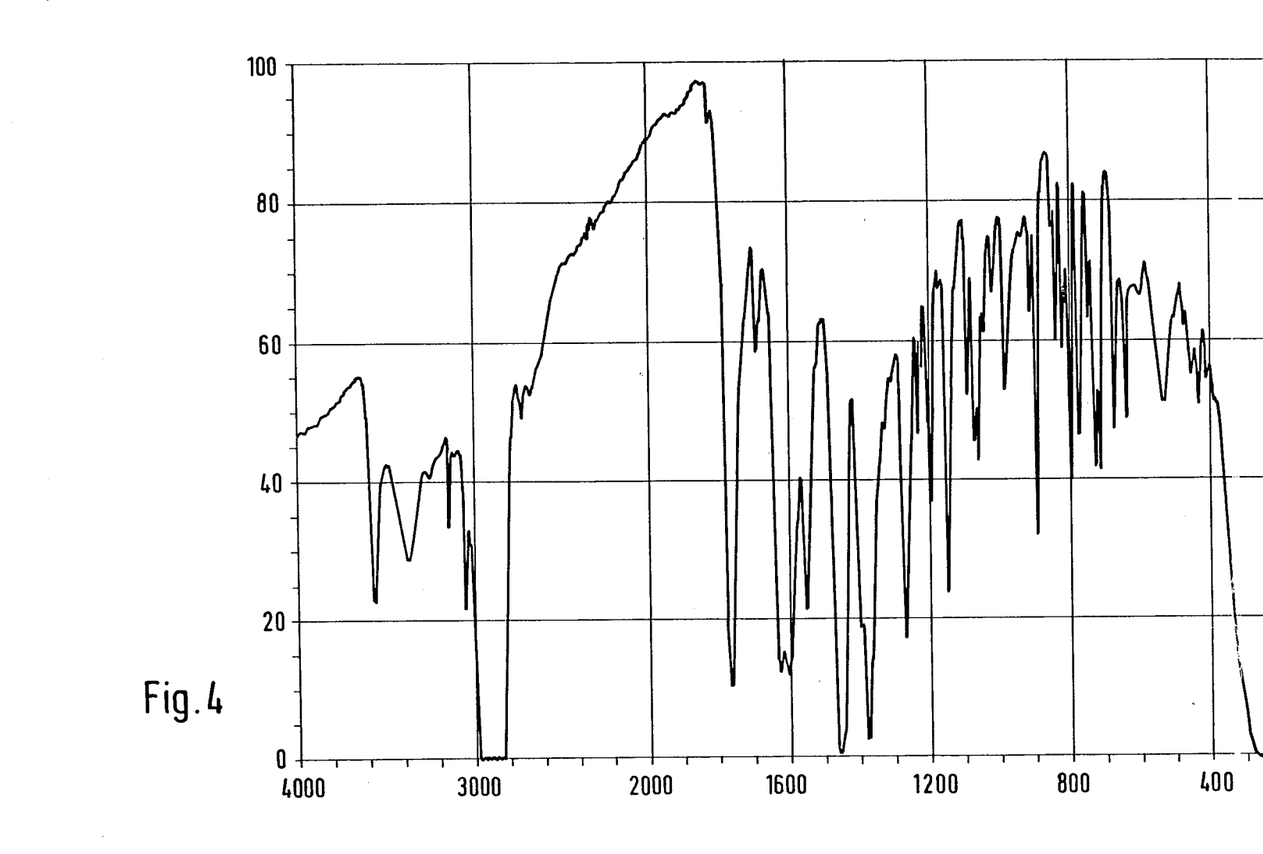

Lithium (5R) (Z)-6-(1-methyl-1,2,3-triazol-4-yl-methylene)penem-3-carboxylate monohydrate A stirred solution of the sodium salt monohydrate (17a) (200 mg) in water (6.5 ml) was treated with lithium chloride (280 mg, 6.6 mmol). After 0.25 hour the solution was cooled to 5° C. After one hour a small amount of solid was present in the solution. The mixture was then stirred at room temperature and a further quantity (420 mg) of lithium chloride was added. Stirring was continued for one hour during which time crystallization occurred. The resulting solid was filtered off and washed with ice-cold water/ethanol (1:1, v/v)(0.25 ml), then ethanol (2 ml), then acetone (2 ml) and finally ether (2 ml). The solid was then air-dried to constant weight to provide the title lithium salt monohydrate (20) (158 mg) as needles; $[\alpha]_D^{20}$ (c 1 in water) +492.3°; $\nu_{max}$ (H$_2$O) 282 nm ($\epsilon_m$ 24,950), 366 (1,950); $\nu_{max}$ (nujol) 3568, 3375, 1765, 1691, 1628,1604 cm$^{-1}$; δ(D$_2$O) 4.14 (3H, s), 6.60 (1H, d, J 1.0 Hz), 7.05 (1H, s), 7.20 (1H, d, J 1.0 Hz), 8.17 (1H, s); (Found C, 41.55; H, 3.01; N, 19.65; S, 11.52. C$_{10}$H$_7$N$_4$O$_3$SLi.H$_2$O requires C, 41.67; H, 3.13; N, 19.44; S, 11.11%). The infra-red spectrum of the product is shown in the accompanying FIG. 4.

EXAMPLE 7

Figure 5:
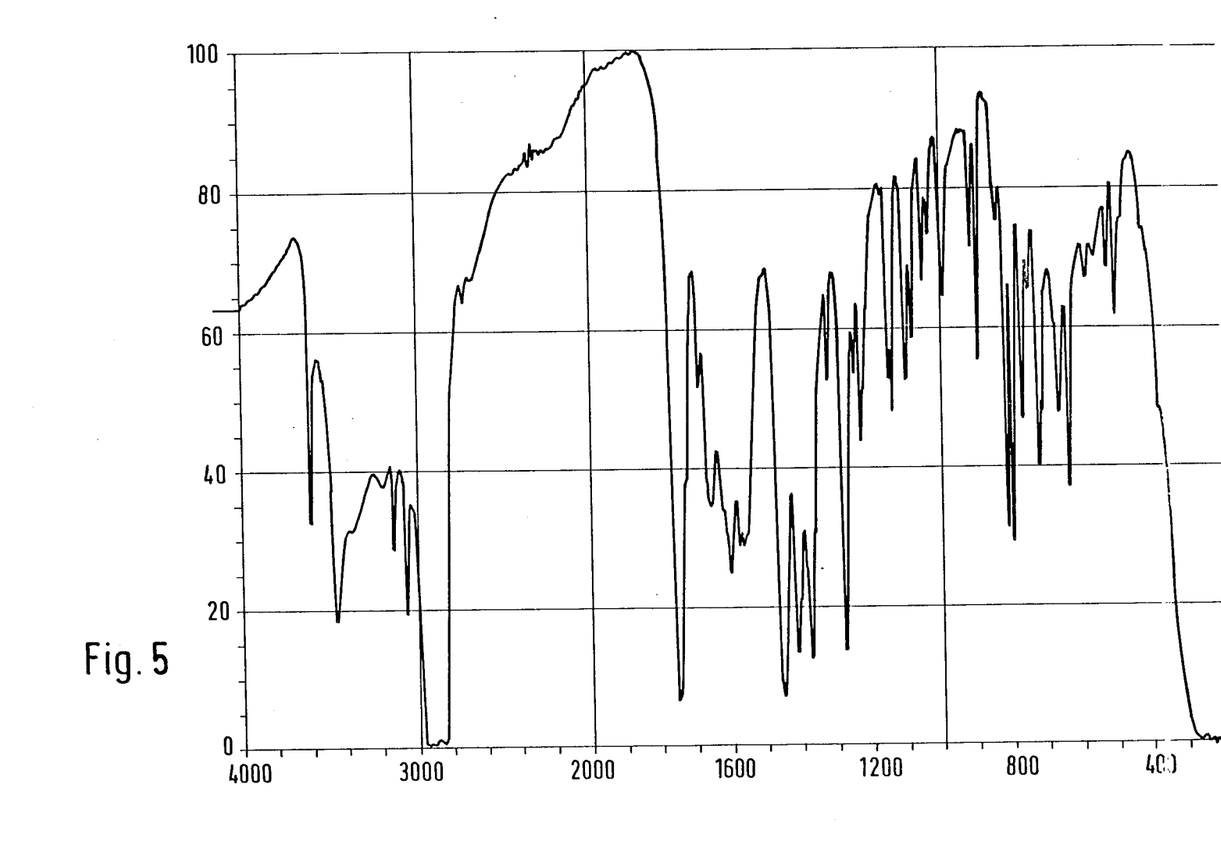

Calcium (5R) (Z)-6-(1-methyl-1,2,3-triazol-4-ylmethylene)penem-3-carboxylate tetrahydrate A solution of the sodium salt monohydrate (17a) (300 mg) in water (150 ml) was covered with methyl isobutyl ketone (150 ml). The vigorously stirred mixture was carefully treated dropwise with 0.1N sulphuric acid solution until a pH of 2.5 was achieved. The organic phase was separated and washed with water. The organic phase was then vigorously stirred and treated dropwise with a solution of calcium ethyl hexanoate in methyl isobutyl ketone (0.21M, 1.9 ml). Within a few minutes a solid was obtained. Water (0.5 ml) was added to the mixture and stirring was continued for another minute. The organic solvent was decanted off, and a further quantity (100 ml) of methyl isobutyl ketone was added. After stirring for another minute the solvent was decanted off. The solid was then stirred with acetone (200 ml) for 30 minutes. The resulting crystalline solid was collected by filtration, washed with acetone and ether and dried to provide the title calcium salt (21) (220 mg) as needles; $[\alpha]_D^{20}$ (c 0.1 in water)+524°; $\nu_{max}$ (H$_2$O) 282 nm ($\epsilon_m$ 49,140), 366 (3435); $\nu_{max}$ (nujol) 3612, 3466, 1757, 1694, 1661, 1604, 1577, 1566 cm$^{-1}$; δ(D$_2$O) 4.16 (3H, s), 6.66 (1H, d, J, 1.0 Hz), 7.09 (1H, s), 7.25 (1H, d, J 1.0 Hz), 8.19 (1H, s); (Found C, 37.71; H, 3.36; N, 17.36; N, 17.34; S, 10.17. C$_{20}$H$_{14}$N$_8$O$_6$S$_2$Ca.4H$_2$O requires C, 37.65; H, 3.48; N, 17.56; S, 10.03%). Its infra-red spectrum is shown in the accompanying FIG. 5.

EXAMPLE 8

Figure 6:
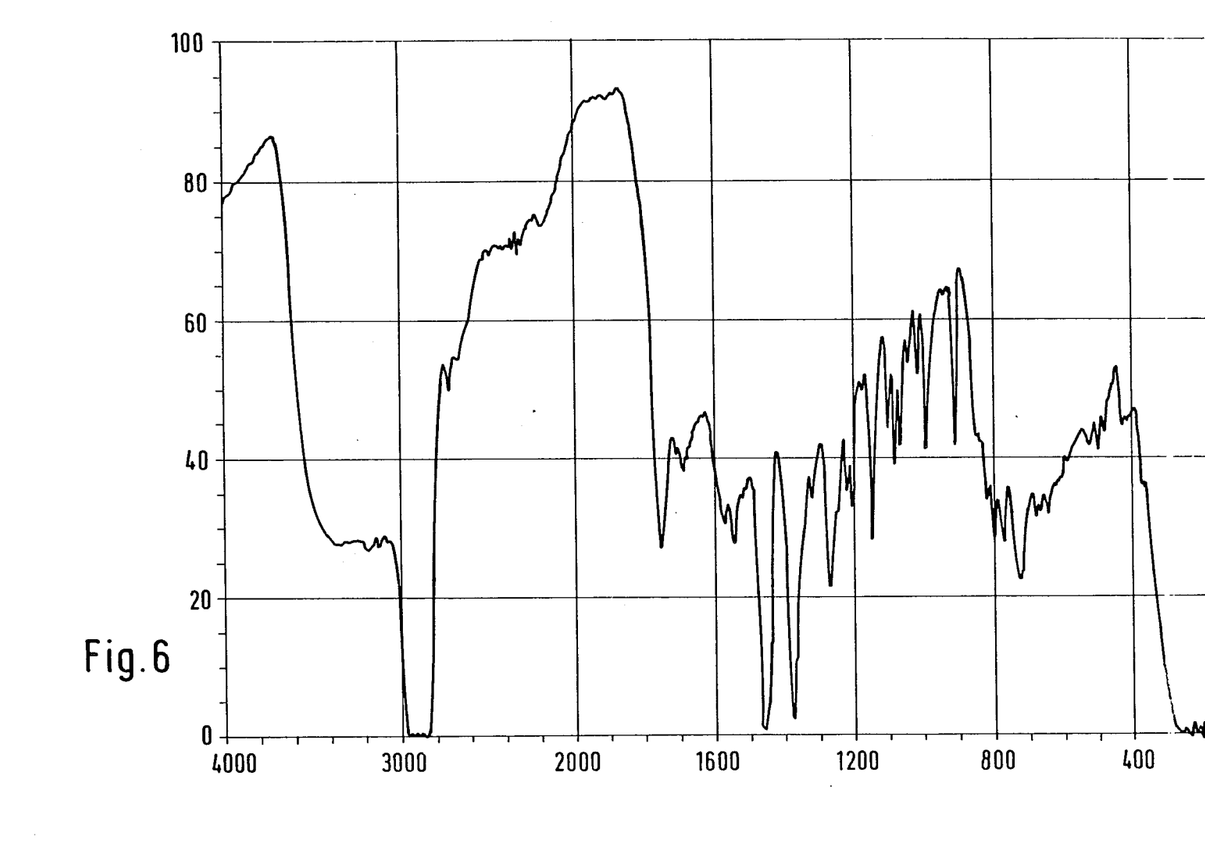

Magnesium (5R)(Z)-6-(1-methyl-1,2,3-triazol-4-ylmethylene)-penem-3-carboxylate dodecahydrate A solution of the sodium salt monohydrate (17a) (304 mg) in water (150 ml) was covered with methyl isobutyl ketone (150 ml). The vigorously stirred mixture was carefully treated dropwise with 0.1N sulphuric acid solution until a pH of 2.5 was achieved. The organic phase was separated and washed with water. The organic phase was then vigorously stirred and treated dropwise with a solution of magnesium ethyl hexanoate in methyl isobutyl ketone (0.21M, 1.9 ml). Within a few minutes a solid was obtained. The solvent was decanted off, more methyl isobutyl ketone (100 ml) was added and after stirring for a minute, the solvent was decanted off. The solid was then treated with acetone (200 ml) and after stirring for a few minutes, water (0.5 ml) was added and stirring continued for a further 30 minutes. The resulting solid was collected by filtration, washed with acetone and ether and dried. This material was then treated with water (120 ml), and the filtered solution was then evaporated to low volume (approx. 1–2 ml). The resulting crystalline solid was collected by filtration, washed with a 1:1 (v/v) ice-cold mixture of acetone and water (1 ml), acetone (2 ml) and ether (3 ml), and dried to provide the title magnesium salt (22) (230 mg) as rhomboids; $[\alpha]_D^{20}$ (c 0.1 in water) +434°; $\nu_{max}$ (H$_2$O) 282 nm ($\epsilon_m$ 49,740), 366 (3,983); $\nu_{max}$ (nujol) 3190 (br) 1752, 1691, 1570, 1545 cm$^{-1}$; δ(D$_2$O) 4.12 (3H, s), 6.63 (1H, d, J 1.0 Hz), 7.05 (1H, s), 7.22 (1H, d, J 1.0 Hz), 8.16 (1H, s); (Found, C, 31.29; H, 4.85; N, 14.57; S, 8.54. C$_{20}$H$_{18}$N$_8$O$_6$S$_2$Mg.12 H$_2$O requires C, 31.33; H, 4.96: N, 14.62: S, 8.36%). Its infra-red spectrum is shown in the accompanying FIG. 6.

EXAMPLE 9

Figure 7:
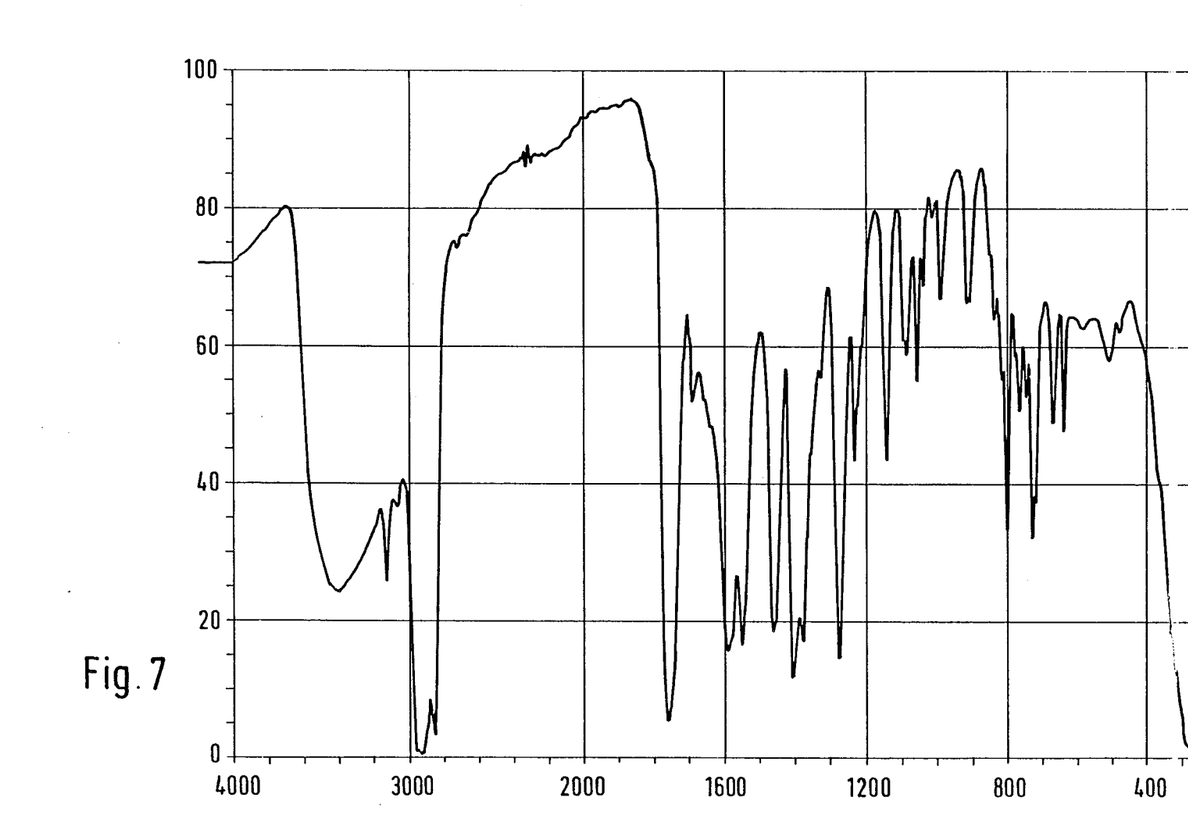

Crystalline barium (5R) (Z)-6-(1-methyl-1,2,3-triazol-4-yl-methylene)-penem-3-carboxylate hydrate A suspension of the free acid (19) (230 mg) in water (30 ml) was treated dropwise with a filtered aqueous solution of barium hydroxide (0.025M) until a pH of 7 was obtained. The solution was filtered and evaporated to approximately 20 ml in volume. The mixture was left at 5° C. for 16 hours, then evaporated to low volume (approx. 5 ml) and treated with acetone (approx. 10 ml). The solid was collected by filtration, washed with acetone and ether and dried to provide the crystalline title barium salt (23) as a hydrate; $[\alpha]_D^{20}$ (c 0.1 in water) 402°; $\nu_{max}$ (H$_2$O) 282 nm, 366; $\nu_{max}$ (nujol) 3394, 1762, 1691, 1589, 1552 cm$^{-1}$; $\delta$(D$_2$O) 4.11 (3H, s), 6.61 (1H, d, 1.0 Hz), 7.04 (1H, s), 7.21 (1H, d, J 1.0 Hz), 8.15 (1H, s); (Found C, 30.83; H, 2.81; N, 14.15; S, 8.47%). Its infrared spectrum is shown in the accompanying FIG. 7.

We claim:

1. (5R) (Z)-6-(1-methyl-1,2,3-triazol-4-yl-methylene)-penem-3-carboxylic acid and salts thereof in analytically pure form.

2. A salt of (5R) (Z)-6-(1-methyl-1,2,3-triazol-4-yl-methylene)-penem-3-carboxylic acid in crystalline form.

3. A salt of (5R) (Z)-6-(1-methyl-1,2,3-triazol-4-yl-methylene)-penem-3-carboxylic acid in the form of a hydrate.

4. A salt of (5R) (Z)-6-(1-methyl-1,2,3-triazol-4-yl-methylene)-penem-3-carboxylic acid in the form of a crystalline hydrate.

5. Crystalline (5R) sodium (Z)-6-(1-methyl-1,2,3-triazol-4-ylmethylene)penem-3-carboxylate.

6. Crystalline (5R) potassium (Z)-6-(1-methyl-1,2,3-triazol-4-ylmethylene)penem-3-carboxylate.

7. Crystalline (5R) calcium (Z)-6-(1-methyl-1,2,3-triazol-4-ylmethylene)-penem-3-carboxylate.

8. Crystalline (5R) magnesium (Z)-6-(1-methyl-1,2,3-triazol-4-ylmethylene)-penem-3-carboxylate.

9. Crystalline (5R) barium (Z)-6-(1-methyl-1,2,3-triazol-4-ylmethylene)-penem-3-carboxylate.

10. (5R) Sodium (Z)-6-(1-methyl-1,2,3-triazol-4-yl-methylene)penem-3-carboxylate in the form of a hydrate.

11. (5R) Sodium (Z)-6-(1-methyl-1,2,3-triazol-4-yl-methylene)penem-3-carboxylate monohydrate.

12. (5R) Potassium (Z)-6-(1-methyl-1,2,3-triazol-4-yl-methylene)penem-3-carboxylate in the form of a hydrate.

13. (5R) Potassium (Z)-6-(1-methyl-1,2,3-triazol-4-yl-methylene)penem-3-carboxylate monohydrate.

14. (5R) Calcium (Z)-6-(1-methyl-1,2,3-triazol-4-yl-methylene)penem-3-carboxylate in the form of a hydrate.

15. (5R) Calcium (Z)-6-(1-methyl-1,2,3-triazol-4-yl-methylene)penem-3-carboxylate tetrahydrate.

16. (5R) Magnesium (Z)-6-(1-methyl-1,2,3-triazol-4-yl-methylene)penem-3-carboxylate in the form of a hydrate.

17. (5R) Magnesium (Z)-6-(1-methyl-1,2,3-triazol-4-yl-methylene)penem-3-carboxylate dodecahydrate.

18. (5R) Barium (Z)-6-(1-methyl-1,2,3-triazol-4-yl-methylene)penem-3-carboxylate in the form of a hydrate.

19. Crystalline (5R) (Z)-6-(1-methyl-1,2,3-triazol-4-yl-methylene)-penem-3-carboxylic acid, free of solvation by ethyl acetate.

20. Crystalline (5R) (Z)-6-(1-methyl-1,2,3-triazol-4-yl-methylene)-penem-3-carboxylic acid, free of solvation by an organic solvent.

21. Crystalline (5R) (Z)-6-(1-methyl-1,2,3-triazol-4-yl-methylene)-penem-3-carboxylic acid in analytically pure form.

22. Crystalline (5R) lithium (Z)-6-(1-methyl-1,2,3-triazol-4-ylmethylene)-penem-3-carboxylate.

23. (5R) Lithium (Z)-6-(1-methyl-1,2,3-triazol-4-yl-methylene)penem-3-carboxylate in the form of a hydrate.

24. (5R) Lithium (Z)-6-(1-methyl-1,2,3-triazol-4-yl-methylene)penem-3-carboxylate monohydrate.

25. A process for the preparation of (5R) (Z)-6-(1-methyl-1,2,3-triazol-4-yl-methylene)penem-3-carboxylic acid or a salt thereof, which comprises crystallising the said acid or salt from an aqueous medium.

26. A process for the purification of (5R) (Z)-6-(1-methyl-1,2,3-triazol-4-yl-methylene) penem-3-carboxylic acid or a salt thereof, which comprises crystallising the said acid or salt from an aqueous medium.

27. A process for the purification of (5R) (Z)-6-(1-methyl-1,2,3-triazol-4-yl-methylene)-penem-3-carboxylic acid or a salt thereof, which comprises acidifying a salt of the said penem in an aqueous medium, and isolating the resulting precipitated penem free acid and, if desired, subsequently converting the penem free acid to a salt thereof.

28. A pharmaceutical composition useful for treating bacterial infections which comprises a compound as claimed in any one of claims 1 to 4 and 5 to 21, in admixture or conjunction with a pharmaceutically acceptable carrier.

29. A method of treating a bacterial infection, which comprises administering to a patient in need thereof a B-lactamase inhibitory amount of a compound as claimed in any one of claims 1 to 4 and 5 to 21.

* * * * *